(12) United States Patent
La et al.

(10) Patent No.: US 12,064,462 B2
(45) Date of Patent: Aug. 20, 2024

(54) COMPOSITION FOR STRESS RELIEF CONTAINING FERMENTED RIPENED NONI AND CALAMANSI EXTRACT AS ACTIVE INGREDIENTS

(71) Applicants: ATOMY OROT CO., LTD., Gongju-si (KR); NSTBIO CO., LTD., Gimpo-si (KR)

(72) Inventors: Im Joung La, Gongju-si (KR); Geum Su Seong, Gimpo-si (KR); Eun Young Park, Gimpo-si (KR); Yong Deok Kim, Gimpo-si (KR); Eun Min Kim, Gimpo-si (KR); Soo Jin Kim, Gimpo-si (KR)

(73) Assignees: ATOMY OROT CO., LTD., Gongju-si (KR); NSTBIO CO., LTD., Gimpo-si (KR)

(*) Notice: Subject to any disclaimer, the term of this patent is extended or adjusted under 35 U.S.C. 154(b) by 0 days.

(21) Appl. No.: 18/300,482

(22) Filed: Apr. 14, 2023

(65) Prior Publication Data
US 2023/0248796 A1 Aug. 10, 2023

Related U.S. Application Data

(62) Division of application No. 17/646,467, filed on Dec. 29, 2021, now Pat. No. 11,911,430.

(30) Foreign Application Priority Data

Dec. 29, 2020 (KR) .................. 10-2020-0185599
Nov. 29, 2021 (KR) .................. 10-2021-0166914

(51) Int. Cl.
| | | |
|---|---|---|
| A61K 36/746 | (2006.01) | |
| A23L 29/00 | (2016.01) | |
| A23L 33/105 | (2016.01) | |
| A61K 36/752 | (2006.01) | |
| A61P 25/22 | (2006.01) | |

(52) U.S. Cl.
CPC .......... *A61K 36/746* (2013.01); *A23L 29/065* (2016.08); *A23L 33/105* (2016.08); *A61K 36/752* (2013.01); *A61P 25/22* (2018.01)

(58) Field of Classification Search
None
See application file for complete search history.

(56) References Cited

FOREIGN PATENT DOCUMENTS

| CN | 101057700 A | 10/2007 |
|---|---|---|
| KR | 10-2005-0049617 A | 5/2005 |
| KR | 10-2009-0072555 A | 7/2009 |
| KR | 10-2047627 B1 | 12/2019 |
| KR | 10-2020-0040205 A | 4/2020 |
| KR | 10-2151372 B1 | 9/2020 |
| PH | 2/2013/000653 | 3/2014 |

OTHER PUBLICATIONS

English translation of Pulmuwon Green Juice Launches Noni & Calamansi, Feb. 2019, Retrieved from Internet: https://www-newstown-co-kr.translate.goog/news/articleView.html?idxno=398766&_x_tr_sl=ko&_x_tr_tl=en&_x_tr_hl=en&_x_tr_pto=sc.*
English translation of Goo (KR 10-2047627 A—Dec. 4, 2019).*
International Search Report dated Apr. 7, 2022 in International Application No. PCT/KR2021/019831.
Office Action dated Mar. 10, 2023 in U.S. Appl. No. 17/646,464.
Medina, P.M.B., et al., "Effect of natural and artificial sweeteners on the hemolymph glucose level (HGL) in *Drosophilia melanogaster*," International Journal of Biosciences, Jul. 14, 2015, 7(1):119-131.
Office Action dated Apr. 18, 2023 in U.S. Appl. No. 17/646,467.
Office Action dated Oct. 19, 2022 in Taiwanese Application No. 110149147.
Screen captures from YouTube video clip entitled "Atomy Organic Fermented Noni Concentrate," 3 pages, uploaded on Nov. 28, 2020. Retrieved from Internet: <https://www.youtube.com/watch?v=O6Rq4x1NJ7M>.
Office Action dated Sep. 1, 2023 in U.S. Appl. No. 17/646,464.
Office Action dated Sep. 6, 2023 in U.S. Appl. No. 17/646,467.
Pulmuwon Green Juice Launches 'Noni & Calamansi', 2019, Retrieved from Internet: of http://www.newstown.co.kr/news/articleView.html? idxno=398766.
Liu, C.-H., et al., "Extraction and Characterization of Antioxidant Compositions From Fermented Fruit Juice of *Morinda citrifolia* (Noni)," Agricultural Sciences in China, Dec. 2007, 6(12):1494-1501.
Office action dated Jan. 26, 2024 in U.S. Appl. No. 17/646,464.
Office Action dated Oct. 13, 2023 in U.S. Appl. No. 18/175,099.

* cited by examiner

*Primary Examiner* — Susan Hoffman
(74) *Attorney, Agent, or Firm* — SALIWANCHIK, LLOYD & EISENSCHENK

(57) ABSTRACT

The present invention relates to a food composition for relieving stress, and specifically, to a food composition for relieving stress, which reduces secretion of the stress hormone cortisol and increases secretion of the happy hormone serotonin by containing fermented and aged noni and calamansi as active ingredients, has no side effects, and is safe for the human body. The composition of the present invention may be used as a health functional food or a pharmaceutical composition. The composition of the present invention has an excellent anti-stress effect.

4 Claims, 6 Drawing Sheets

COMPOSITION FOR STRESS RELIEF CONTAINING FERMENTED RIPENED NONI AND CALAMANSI EXTRACT AS ACTIVE INGREDIENTS

CROSS-REFERENCE TO RELATED APPLICATIONS

This application is a divisional of U.S. application Ser. No. 17/646,467, filed Dec. 29, 2021, now U.S. Pat. No. 11,911,430, which claims the benefit of Korean Application Nos. 10-2020-0185599, filed Dec. 29, 2020; and 10-2021-0166914, filed Nov. 29, 2021; the entire contents of which are incorporated herein by reference.

BACKGROUND

1. Technical Field

The present invention relates to a composition containing fermented and aged noni and a calamansi extract as active ingredients, and more particularly, to a composition capable of relieving stress and inhibiting and alleviating stress-induced symptoms by containing fermented and aged noni and a calamansi extract as active ingredients.

2. Related Art

Stress, which is called the root of all diseases, exists in all areas of life of humans and animals. Stress is a powerful stimulus, is induced by various factors ranging from trivial things experienced in daily life to major events that have a big impact. Stimulation by such stress induces fatigue, malaise, depression, and the like, and causes internal and external negative reactions.

In general, if the stimulus on the body exceeds a certain degree, it causes damage to the body, and in this case, the living body shows a non-specific general adaptive syndrome in response to a certain threat regardless of the type of stimulus, and this phenomenon is called stress (Selye, H.: The stress of life, Toronto, Longnans Green and Co., pp. 1-50, 1958). Such stress causes various detrimental effects, such as tension headache, migraine, hypertension, indigestion, fatigue, pain, menopausal disorders, hair loss, and rough skin. In addition, if stress continues chronically, it may cause various neuroses and gastric ulcers, reduce the physiological activity and immune activity of the body, impair mental activity, and make emotions unstable, resulting in abnormal behavior.

In particular, in modern society, stress excessively occurs, and thus stress has become a very important social problem.

It is known that the causes of stress and the changes in the body thereby are diverse, but stress commonly causes hyperactivity of the hypothalamic-pituitary-adrenal (HPA) axis, which is the sympathetic nervous system, to induce hormone secretion, which causes hyperactivity of the adrenal gland and hypofunction of the spleen, resulting in stress-induced symptoms. If stress is added, the weight of the spleen is significantly reduced due to the decline in immune function, hyperactivity of the adrenal gland is caused by adrenocorticotropic hormone and the weight thereof is increased, lipid reduction occurs, and the secretion of cortisol is promoted. The amount of cortisol tends to increase with age and stress, which also contributes to obesity. In addition, if stress is added, the adrenal glands secrete hormones, resulting in increases in cholesterol, glucose, and lactate dehydrogenase (LDH) levels in the blood.

Meanwhile, it is known that, in the case of gastric ulcers that are deeply related to stress, reactive oxygen species are involved in the formation of ulcers. Biological defense systems for removing reactive oxygen species (ROSs) are broadly classified into enzymatic defense systems including enzymes such as superoxide dismutase (SOD), catalase, and glutathione peroxidase, and non-enzymatic defense systems that stops or terminates the chain reaction of ROSs or free radicals. Organisms using oxygen have SOD, which is an enzyme that removes superoxide, and thus the living body is protected from damage by superoxide. Catalase functions to protect the living body by removing $H_2O_2$ generated by the enzymatic reaction of SOD or the like in tissue. In addition, it has been reported that catalase can not only remove free radicals of reactive oxygen species generated during the metabolic process, but also be irreversibly inactivated by these reactive oxygen species, and also removes free radicals generated by fatty acid oxidation. Glutathione (GSH), which is the most prevalent non-protein thiol in animal tissues, serve as a free radical scavenger and as a substrate for GSH-Px that metabolizes $H_2O_2$ and lipid peroxide, and plays an important role as an intracellular antioxidant (Cho SY. et al., J. Korean Soc. Food Sci. Nutr., 32(3), pp. 458-463, 2003).

In recent years, various methods have been devised to relieve stress, and the most effective method is exercise or psychotherapy. In addition, there are methods for minimizing damage caused by stress by performing drug therapy depending on the intensity of stress. In particular, drugs that are used to relieve stress include psychotropic drugs such as benzodiazepines, which are nerve stabilizers, and tranquilizer which are mental stabilizers.

However, when the above-described stabilizers are used for stress relief, problems arise in that there is a risk of addiction and it is difficult to exclude side effects, due to the characteristics of the synthetic drugs. Excessive dependence on drugs has a negative side in that it can cause other stress.

In recent years, various attempts have been made to develop foods for recovering from fatigue or relieving stress using herbal medicinal materials.

As studies on compositions for recovering from fatigue using natural herbal medicinal materials, Korean Patent Application Publication No. 2000-0066777 discloses a functional beverage containing extracts from *Cnidium officinale*, licorice, *Puerariae* radix, *Hovenia dulcis* fruit, *Alnus japonica*, *Citrus unshiu* peel, *Zizyphi fructus*, *Oenanthe javanica*, and ginkgo leaf, and Korean Patent Application Publication No. 10-2005-0108856 discloses a medicinal herbal drink for recovering from fatigue containing *Polygonatum sibiricum* rhizome, *Liriope platyphylla*, *Hovenia dulcis* fruit, and *Schisandra chinensis* fruit.

As studies on foods for relieving stress, Korean Patent Application Publication No. 10-2004-0006705 discloses a health supplement food containing, as essential ingredients, deep water, organic germanium, *Cyperus rotundus*, *Citrus unshiu* peel, malt, *Zizyphi spinosae* semen, and jujube, and Korean Patent Application Publication No. 10-2004-0018888 discloses a food for relieving stress containing, as active ingredients, red *ginseng*, *Gastrodiae rhizome*, and *Rehmannia glutinosa* juice. In addition, Korean Patent Application Publication No. 10-2005-0080455 discloses Kami-sagunga-tang having an anti-stress effect, which contains, in addition to conventional Sagunga-tang, plum, Solomon's seal, *Puerariae* radix, and cinnamon extracts.

It has been found that plants existing in nature contain large amounts of functional ingredients having bioregulatory functions, such as prevention of diseases and suppression of aging. Thus, studies on natural food materials have been actively conducted.

Therefore, in recent years, studies have been actively conducted to develop functional supplements using natural products with guaranteed safety, such as plant extracts. Accordingly, the present inventors have conducted intensive studies on fermented and aged noni and calamansi, and as a result, have found that intake of a complex of fermented and aged noni and calamansi is effective in relieving stress, thereby completing the present invention.

PRIOR ART DOCUMENTS

Patent Documents (Patent Document 1) Korean Patent Application Publication No. 2000-0066777
(Patent Document 2) Korean Patent Application Publication No. 10-2005-0108856

SUMMARY

An object of the present invention is to solve the above-described problems and other problems related thereto.

The present inventors have conducted studies on a composition comprising natural ingredients capable of effectively relieving stress, and as a result, have found that a composition containing a complex of fermented and aged noni and a calamansi extract has a stress relief activity, thereby completing the present invention.

An object of the present invention is to provide a composition for relieving stress containing, as active ingredients, fermented and aged noni or an extract thereof and a calamansi extract.

Another object of the present invention is to provide a method for producing a composition containing, as active ingredients, fermented and aged noni or an extract thereof and a calamansi extract.

Still another object of the present invention is to provide a food composition for relieving stress containing, as active ingredients, fermented and aged noni or an extract thereof and a calamansi extract.

Yet another object of the present invention is to provide a pharmaceutical composition for relieving stress containing, as active ingredients, fermented and aged noni or an extract thereof and a calamansi extract.

Still yet another object of the present invention is to provide a quasi-drug composition for relieving stress containing, as active ingredients, fermented and aged noni or an extract thereof and a calamansi extract.

A further object of the present invention is to provide a feed composition for relieving stress containing, as active ingredients, fermented and aged noni or an extract thereof and a calamansi extract.

The objects to be achieved according to the technical idea of the present invention disclosed in the present specification are not limited to the above-mentioned objects, and other objects not mentioned herein will be clearly understood by those skilled in the art from the following description.

The present invention will be described in detail below. Meanwhile, each description and embodiment disclosed in the present application may be applied to each other description and embodiment. That is, all combinations of various components disclosed in the present application fall within the scope of the present application. In addition, the scope of the present application is not construed as being limited by the detailed description described below.

To achieve the above-described objects, the present invention provides a composition for relieving stress or inhibiting or treating stress-induced diseases containing, as active ingredients, fermented and aged noni or an extract thereof and a calamansi extract.

Hereinafter, the present invention will be described in more detail.

As used herein, the term "fermented and aged noni" refers to noni obtained by fermenting and aging noni inoculated with lactic acid bacteria. Here, the part of noni that is used in the present invention is not limited, but noni fruits may be used as an example.

In the present invention, "fermented noni" may be a fermented product obtained by fermenting noni fruits inoculated with any one or more of the following 7 types of lactic acid bacteria:
(1) *Lactobacillus plantarum*;
(2) *Lactobacillus paracasei*;
(3) *Lactobacillus rhamnosus*;
(4) *Lactobacillus casei*;
(5) *Lactobacillus fermentum*;
(6) *Lactobacillus reuteri*; and
(7) *Lactococcus lactis* subsp. *lactis*.

The "fermented noni" may be obtained by fermenting noni using lactic acid bacteria having excellent bioconversion ability so that the glycoside compounds scopolin and asperuloside contained in the noni may be bioconverted to the non-glycoside compounds scopoletin, deacetylasperulosidic acid (DAA) and asperulosidic acid.

The content of bioconverted scopoletin in the "fermented noni" is 1 to 200 μg/mL, the content of deacetylasperulosidic acid in the fermented noni is 0.2 to 0.6 mg/mL, and the content of asperulosidic acid in the fermented noni is 0.096 to 1.41 mg/mL. The contents of scopoletin, deacetylasperulosidic acid and asperulosidic acid in the fermented noni are equal to those in fermented and aged noni within analysis errors.

In the present invention, "fermented and aged noni" may be fermented and aged noni itself or an extract obtained therefrom.

As an example, the fermented and aged noni of the present invention may be obtained by fermenting and aging noni fruits inoculated with lactic acid bacteria, and the liquid obtained by squeezing the fermented and aged noni may be an extract.

Calamansi is a tropical fruit that is grown in Southeast Asia. The term "calamansi extract" means a fruit juice extracted from calamansi, and the method of obtaining the fruit juice by extraction is well known in the art, and thus detailed description thereof will be omitted. In addition, it is also possible to purchase and use a commercially available undiluted calamansi extract, rather than to prepare the extract separately. Calamansi has a 30 times higher vitamin C content than lemon, and contains large amounts of cryptoxanthin, hesperidin, nobiletin, cinehulin, and the like.

As used herein, the term "extract" commonly refers to a crude extract in the art, but in a broad sense also refers to a fraction obtained by fractionating the extract. That is, the fermented and aged noni extract or the calamansi extract includes not only one obtained using an extraction solvent, but also one obtained by subjecting the obtained one to a purification process. For example, the fermented and aged noni extract or calamansi extract of the present invention also includes a fraction obtained by passing the extract through an ultrafiltration membrane with a predetermined molecular weight cut-off value, or a fraction obtained by additionally performing various purification methods such as various chromatography methods (designed for separation according to size, charge, hydrophobicity, or hydrophilicity).

In the present specification, the expression "containing as active ingredients" means containing an amount sufficient to achieve the efficacy or activity of each of the fermented and aged noni or an extract thereof and the calamansi extract. In the present invention, since a composition containing an extract of each of the fermented and aged noni and calamansi, which are natural plant materials, and has no side effects on the human body even when the extracts are administered in excessive amounts, the upper limit of the amount of each of the fermented and aged noni extract and calamansi extract contained in the composition of the present invention may be selected within an appropriate range by those skilled in the art.

Each of the fermented and aged noni extract and calamansi extract according to the present invention is obtained by extraction using an organic solvent, and examples of an extraction solvent that may be used in the present invention are as follows.

First, suitable examples of polar solvents include (i) water, (ii) an alcohol having 1 to 6 carbon atoms (preferably, methanol, ethanol, propanol, butanol, n-propanol, iso-propanol, n-butanol, 1-pentanol, 2-butoxyethanol or ethylene glycol), (iii) acetic acid, (iv) DMFO (dimethyl formamide), and (v) DMSO (dimethyl sulfoxide).

Suitable examples of nonpolar solvents include acetone, acetonitrile, ethyl acetate, methyl acetate, fluoroalkane, pentane, hexane, 2,2,4-trimethylpentane, decane, cyclohexane, cyclopentane, diisobutylene, 1-pentene, 1-chlorobutane, 1-chloropentane, o-xylene, diisopropyl ether, 2-chloropropane, toluene, 1-chloropropane, chlorobenzene, benzene, diethyl ether, diethyl sulfide, chloroform, dichloromethane, 1,2-dichloroethane, aniline, diethylamine, ether, carbon tetrachloride, methylene chloride, petroleum ether, and THF.

Preferred examples of an extraction solvent that may be used in the present invention include (a) water, (b) an anhydrous or lower alcohol having 1 to 4 carbon atoms (e.g., methanol, ethanol, propanol, butanol, etc.), (c) a mixture of the lower alcohol and water, (d) acetone, (e) ethyl acetate, (f) chloroform, (g) butyl acetate, (h) 1,3-butylene glycol, (i) hexane, and (j) diethyl ether. For easy extraction, extraction may be performed using water, ethanol, or a mixture of water and ethanol.

In addition, each of the fermented and aged noni or an extract thereof and the calamansi extract, which are used in the present invention, may be produced in a powder form by additional processes such as distillation under reduced pressure and freeze-drying or spray-drying.

In the present invention, the fermented and aged noni or an extract thereof and the calamansi extract may be contained at a weight ratio of 70:30 to 99:1, or 80:20 to 95:5, or 70:30 to 90:10.

According to one aspect of the present invention, the present invention is directed to a food composition for relieving stress containing, as active ingredients, fermented and aged noni or an extract thereof and a calamansi extract.

The food composition may include, for example, a health functional food composition. Examples of the health functional food composition include various foods, beverages, gum, tea, vitamin complexes, health supplements, etc. The health functional food composition may be used in the form of powders, granules, pills, tablets, capsules, candies, syrups or beverages. The food composition of each formulation may contain, in addition to the active ingredient, ingredients commonly used in the art, which may be appropriately selected by those skilled in the art without difficulty depending on the formulation or intended use of the composition. When the food composition is applied simultaneously with other raw materials, a synergistic effect may occur.

The composition may contain other ingredients, which may impart a synergistic effect to the main effect, within a range that does not impair the main effect of the present invention. For example, the composition may further contain additives such as fragrance, a colorant, a bactericide, an antioxidant, a preservative, a humectant, a thickener, an inorganic salt, an emulsifier, and a synthetic polymer, in order to improve physical properties thereof.

When the health functional food composition of the present invention is used as a food additive, the fermented and aged noni or an extract thereof and the calamansi extract may be added as they are or used together with other foods or food ingredients, and may be appropriately used according to a conventional method. The content of each of the active ingredients may be suitably determined according to the intended use (prevention, health improvement or therapeutic treatment). The food is not particularly limited in the kind thereof. Examples of food to which the fermented and aged noni or an extract thereof and the calamansi extract may be added include meat, sausage, bread, chocolate, candy, snacks, confectionery, pizza, ramen, other noodles, gums, dairy products including ice cream, various soups, beverages, teas, drinks, alcoholic beverages, vitamin complexes, etc., and include all health functional foods in the ordinary sense.

When the composition of the present invention is used as a health drink, it may contain various flavoring agents or natural carbohydrates as additional ingredients, like a conventional drink. Examples of the above-described natural carbohydrates include monosaccharides such as glucose and fructose, disaccharides such as maltose and sucrose, polysaccharides such as dextrin and cyclodextrin, and sugar alcohols such as xylitol, sorbitol and erythritol. As the flavoring agents, there may be used natural flavoring agents such as thaumatin or *stevia* extract, or synthetic flavoring agents such as saccharin or aspartame.

The present invention provides a method for producing a composition containing fermented and aged noni and calamansi, the method comprising steps of: obtaining fermented and aged noni by fermenting and aging noni using lactic acid bacteria; and adding and mixing calamansi with the fermented and aged noni.

According to one aspect of the present invention, the present invention provides a method for producing a composition containing fermented and aged noni or an extract thereof and a calamansi extract, the method comprising steps of: (a) obtaining fermented and aged noni by fermenting and aging noni using lactic acid bacteria; and (b) adding calamansi to the fermented and aged noni, followed by aging.

According to one aspect of the present invention, the present invention provides a method for producing a composition for relieving stress, the method comprising steps of: (a) producing bioconverted fermented and aged noni by fermenting and aging noni fruits inoculated with lactic acid bacteria; (b) squeezing the fermented and aged noni; and (c) adding and mixing calamansi with the fermented and aged noni.

The fermentation and aging may be performed at 35 to 40° C. for 48 to 168 hours.

The aging may be performed by pouring the fermentation broth, produced in the fermentation process, over the fermentation product at regular time intervals.

The bioconverted fermented and aged noni may be a fermented product obtained by fermenting noni fruits inoculated with any one or more of the above-described 7 types of lactic acid bacteria.

According to one aspect of the present invention, the present invention is directed to a pharmaceutical composition for relieving stress or inhibiting or treating stress-induced diseases containing, as active ingredients, fermented and aged noni or an extract thereof and a calamansi extract.

In an example of the present invention, it was confirmed that, when the pharmaceutical composition of the present invention was used, the secretion of the stress hormone cortisol was suppressed. Thus, it can be seen that the pharmaceutical composition of the present invention may also inhibit stress-induced behavioral changes, and thus exhibit the effect of inhibiting or treating stress-induced diseases such as depression, anxiety disorder, fatigue syndrome, sleep disorder, panic disorder, memory loss, lethargy, insomnia, Parkinson's disease, and Alzheimer's disease.

Therefore, the present invention is directed to a pharmaceutical composition for inhibiting or treating stress-induced diseases containing, as active ingredients, fermented and aged noni or an extract thereof and a calamansi extract.

The pharmaceutical composition according to the present invention may contain the active ingredients alone or may be formulated in a suitable form together with a pharmaceutically acceptable carrier, and may further contain an excipient or a diluent. As used herein, the term "pharmaceutically acceptable" refers to a non-toxic composition which is physiologically acceptable and, when administered to the human beings, does not cause allergic reactions such as gastrointestinal disorders and dizziness, or similar reactions.

The pharmaceutical composition may further contain a pharmaceutically acceptable carrier such as a carrier for oral administration or a carrier for parenteral administration. Examples of the carrier for oral administration include lactose, starch, cellulose derivatives, magnesium stearate, stearic acid, and the like. In addition, various drug delivery materials that are used for oral administration of peptide formulations may be included. In addition, examples of the carrier for parenteral administration include water, suitable oil, saline, aqueous glucose and glycol, and the like, and further include a stabilizer and a preservative. Suitable stabilizers include antioxidants such as sodium hydrogen sulfite, sodium sulfite or ascorbic acid. Suitable preservatives include benzalkonium chloride, methyl- or propylparaben and chlorobutanol. The pharmaceutical composition of the present invention may further contain a lubricant, a wetting agent, a sweetening agent, a flavoring agent, an emulsifying agent, a suspending agent, and the like, in addition to the above-described ingredients. Other pharmaceutically acceptable carriers and agents may refer to those described in Remington's Pharmaceutical Sciences, 19th ed., Mack Publishing Company, Easton, PA, 1995.

The composition of the present invention may be administered to mammals including humans by any method. For example, the composition may be administered orally or parenterally. Parenteral administration methods include, but are not limited to, intravenous, intramuscular, intraarterial, intramedullary, intrathecal, intracardiac, transdermal, subcutaneous, intraperitoneal, intranasal, enteral, topical, sublingual or rectal administration.

The pharmaceutical composition of the present invention may be formulated in an oral dosage form or a parenteral dosage form depending on the administration route as described above.

For oral dosage forms, the composition of the present invention may be formulated into a powder, granule, tablet, pill, dragee, capsule, liquid, gel, syrup, slurry, suspension, etc. using methods known in the art. For example, the oral dosage form may be obtained as a tablet or dragee by mixing the active ingredient with a solid excipient, pulverizing the mixture, adding a suitable adjuvant thereto, and processing the mixture into a granule mixture. Examples of suitable excipients include sugars such as lactose, dextrose, sucrose, sorbitol, mannitol, xylitol, erythritol and maltitol, starches such as corn starch, wheat starch, rice starch and potato starch, celluloses such as cellulose, methyl cellulose, sodium carboxymethyl cellulose and hydroxypropylmethyl cellulose, and fillers such as gelatin and polyvinylpyrrolidone. In addition, if necessary, cross-linked polyvinylpyrrolidone, agar, alginic acid or sodium alginate may be added as a disintegrant. Furthermore, the pharmaceutical composition of the present invention may further contain an anti-aggregating agent, a lubricant, a wetting agent, a flavoring agent, an emulsifying agent, and a preservative.

For parenteral dosage forms, the pharmaceutical composition may be formulated in the form of an injection, cream, lotion, external ointment, oil, humectant, gel, aerosol or nasal inhalant by methods known in the art. These formulations are described in Remington's Pharmaceutical Science, 19$^{th}$ ed., Mack Publishing Company, Easton, PA, 1995, which is a prescription commonly known in all pharmaceutical chemistries.

The total effective amount of the composition of the present invention may be administered to a patient in a single dose, and may be administered in multiple doses by a fractionated treatment protocol over a prolonged period of time. The pharmaceutical composition of the present invention may have varying contents of the active ingredient depending on the severity of the disease. Preferably, the preferred total dose of the pharmaceutical composition of the present invention may be about 0.01 μg to 10,000 mg, preferably 0.1 μg to 500 mg, most preferably 100 mg to 500 mg per kg of patient body weight per day. However, the effective dose of the pharmaceutical composition to be administered to a patient is determined in consideration of various factors, including the formulation method, the route of administration and the number of treatments, as well as the patient's age, weight, health status and sex, the severity of the disease, diet, and excretion rate, and thus those of ordinary skill in the art will be able to determine an appropriate effective dosage of the composition of the present invention in consideration of these factors. The pharmaceutical composition according to the present invention is not particularly limited in its formulation, administration route and administration method, as long as it exhibits the effect of the present invention.

According to one aspect of the present invention, the present invention is directed to a quasi-drug composition for relieving stress or inhibiting or treating stress-induced diseases containing, as active ingredients, fermented and aged noni or an extract thereof and a calamansi extract.

As used herein, the term "quasi-drug" refers to a product which, among the products being used for the purpose of treatment, alleviation, handling, or prevention of human or animal diseases, excludes those which are not a tool, a machine, or a device, and a product which, among the products being used for the purpose of rendering a pharmacological effect on the human or animal structures and functions, excludes those which are not a tool, a machine, or a device. In one embodiment, the quasi-drug may include an agent for internal administration, but is not limited thereto, and the formulation method, dose, use method, components, etc. of the quasi-drug may be appropriately selected using conventional techniques known in the art.

The quasi-drug composition of the present invention may further contain, in addition to the above ingredient, a pharmaceutically acceptable carrier, excipient or diluent, if necessary. The pharmaceutically acceptable carrier, excipient or diluent is not limited as long as it does not impair the effects of the present invention, and examples thereof include a filler, an extender, a binder, a wetting agent, a disintegrant, a surfactant, a lubricant, a sweetener, a fragrance, and a preservative.

According to one aspect of the present invention, the present invention is directed to a feed composition for relieving stress or inhibiting or treating stress-induced diseases containing, as active ingredients, fermented and aged noni or an extract thereof and a calamansi extract.

In the present invention, the feed composition may be formulated in a conventional feed form, and may also contain known feed ingredients. In addition, the feed composition may be used as a feed additive, which is added in the form of an additive to the feed used. The feed additive of the present invention corresponds to a supplementary feed under the Feed Management Act, and may further contain minerals such as sodium bicarbonate (soda), bentonite, magnesium oxide, and composite minerals, trace minerals such as zinc, copper, cobalt, and selenium, vitamins such as carotene, vitamin E, vitamins A, D, E, nicotinic acid, and vitamin B complexes, protective amino acids such as methionine and lysine, protective fatty acids such as fatty acid calcium salts, live bacteria such as probiotics (lactic acid bacteria), yeast cultures, and fungal fermentation products, yeast agents, etc.

The feed or feed additive of the present invention may be applied to diets for a number of animals, including mammals, poultry and fish.

The fermented and aged noni or extract thereof and calamansi extract contained in the composition for relieving stress according to the present invention may be used as a natural pharmaceutical composition or food composition, and has the effects of relieving stress and inhibiting or efficiently alleviating stress-induced symptoms (diseases) without side effects.

In addition, the fermented and aged noni contains bioconverted components (scopoletin, deacetylasperulosidic acid and asperulosidic acid), which are obtained in the process of fermenting noni fruits and are capable of improving digestion and absorption, and thus it promotes digestion, absorption, and bowel movement in adults and the elderly who have relatively low digestibility. In addition, since the fermented and aged noni is a natural raw material, it has no toxicity or side effects and may be safe to consume.

In addition, the process of producing the fermented and aged noni is simple, and thus may greatly reduce the production cost, thereby greatly reducing the cost burden of consumers.

In addition, the composition containing the complex of the fermented and aged noni and the calamansi extract has improved sensory characteristics compared to conventional noni, and thus is a food composition that consumers can enjoy without burden.

DETAILED DESCRIPTION

Figure 1:
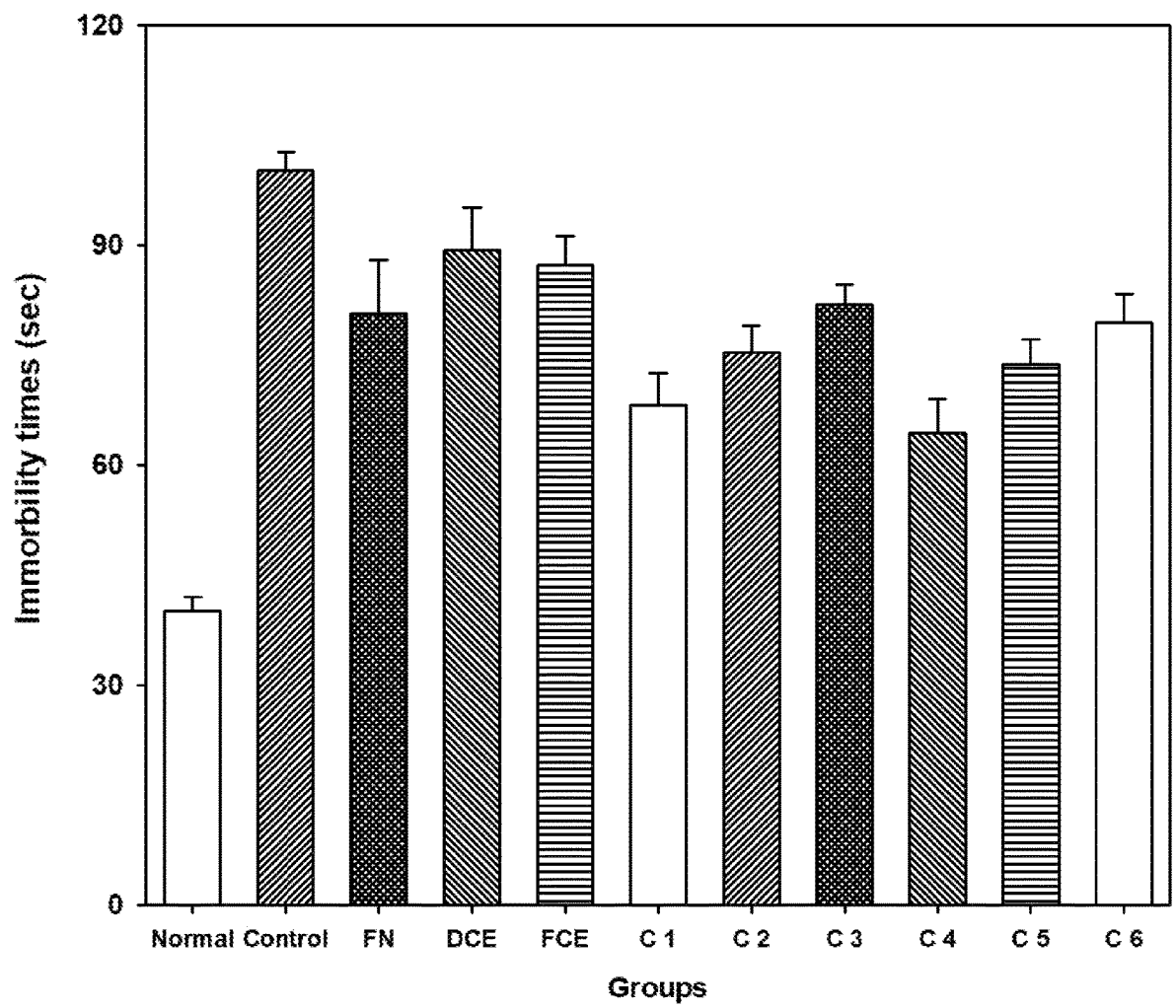
FIG. 1 is a graph showing the results of measuring the immobility times of experimental animals in a forced swimming test after intake of each of a control, a fermented and aged noni extract, a calamansi extract, and complexes of the fermented and aged noni extract and the calamansi extract in an experimental example of the present invention.

Hereinafter, the present invention will be described in more detail with reference to the following examples. However, these examples serve merely to illustrate the present invention, and the scope of the present invention is not limited to these examples.

Example 1: Production of Compositions for Relieving Stress

Compositions according to the present invention were produced through the following process.

1.1: Production of Fermented and Aged Noni 690 kg of noni fruits were inoculated with complex lactic acid bacteria (a complex of 7 types of lactic acid bacteria, AON1805, Lactomason Co., Ltd.) and fermented at 37° C. for 45 days or more. Fermentation and aging were performed while 10 L of the fermentation broth collected every 7 days from the start date of fermentation was poured over the noni fruits. The composition of the complex lactic acid bacteria (a complex of 7 types of lactic acid bacteria, AON1805, Lactomason Co., Ltd.) used is shown in Table 1 below.

After completion of the aging, the fermented and aged noni was squeezed and the solid was removed, thus obtaining a fermented and aged noni extract.

TABLE 1

Raw material name or ingredient name and mixing ratio

| No. | Raw material name or ingredient name | Mixing ratio (%) |
|---|---|---|
| 1 | Lactobacillus plantarum | 70% |
| 2 | Lactobacillus rhamnosus | 5% |
| 3 | Lactobacillus casei | 5% |
| 4 | Lactobacillus fermentum | 5% |
| 5 | Lactobacillus paracasei | 5% |
| 6 | Lactobacillus reuteri | 5% |
| 7 | Lactococcus lactis subsp. lactis | 5% |

1.2: Production of Calamansi Extract

As calamansi, calamansi sold in the market was purchased and used in this Example. As frozen or dried calamansi, frozen or dried calamansi sold in the market was purchased and used.

The frozen calamansi was pulverized and squeezed, thus producing an extract. Meanwhile, 100 g of the dried calamansi was extracted twice at 50° C. for 8 hours after a 10-fold amount (weight) of water was added thereto, and then the extract was filtered through filter paper. The filtrate was dried using a rotary vacuum evaporator (EYELA A-1000S, Tokyo Rikakikai Co., Tokyo, Japan) on a water bath at 37 to 40° C. to remove water, thus producing an extract, which was used as a sample.

The yields of the calamansi extract samples obtained using different extraction solvents are shown in Table 2 below.

TABLE 2

| Sample | Extract | Yield (%) |
|---|---|---|
| Dried calamansi extract (DCE) | Water extract | 13.2 |
| Frozen calamansi extract (FCE) | Squeezed extract | 15.3 |

1.3: Production of Complexes Using Fermented and Aged Noni Extract and Calamansi Extract The fermented and aged noni extract produced in Example 1.1 and the calamansi extract produced in Example 1.2 were mixed together at various ratios and then aged for 15 days to obtain complexes.

[Complex Production]

Complex 1: 90 wt % fermented and aged noni extract: 10 wt % dried calamansi extract Complex 2: 80 wt % fermented and aged noni extract: 20 wt % dried calamansi extract Complex 3: 70 wt % fermented and aged noni extract: 30 wt % dried calamansi extract Complex 4: 90 wt % fermented and aged noni extract: 10 wt % frozen calamansi extract Complex 5: 80 wt % fermented and aged noni extract: 20 wt % frozen calamansi extract Complex 5: 70 wt % fermented and aged noni extract: 30 wt % frozen calamansi extract Experimental Example 1: Evaluation of the Effect of Composition of Present Invention on Stress Relief An evaluation was performed of the stress relief effects of the fermented and aged noni extract produced in Example 1.1, the calamansi extract produced in Example 1.2, and the complexes produced in Example 1.3.

(1) Experimental Mice 4-week-old ICR mice (Orient Bio, Korea) were adapted for 1 week at a temperature of 18° C. to 23° C. and a humidity of 60% with a 12-hr light/12-hr dark cycle. Then, the experimental animals were divided into experimental groups (8 mice per group) as follows. The mice were fed solid feed, and allowed to access feed and water ad libitum, except for the process of inducing stress.

Experimental group 1 (normal control group, hereinafter referred to as Normal); experimental group 2 (negative control group; hereinafter referred to as Control); experimental group 3 (a group to which 100 mg/kg of the fermented and aged noni was administered; hereinafter referred to as FN); experimental group 4 (a group to which 100 mg/kg of the dried calamansi extract was administered; hereinafter referred to as DCE); experimental group 5 (a group to which 100 mg/kg of the frozen calamansi extract was administered; hereinafter referred to as FCE); experimental group 6 (a group to which 100 mg/kg of complex 1 was administered; hereinafter referred to as C 1), experimental group 7 (a group to which 100 mg/kg of complex 2 was administered; hereinafter referred to as C 2); experimental group 8 (a group to which 100 mg/kg of complex 3 was administered; hereinafter referred to as C 3); experimental group 9 (a group to which 100 mg/kg of complex 4 was administered; hereinafter referred to as C 4); experimental group 10 a group to which 100 mg/kg of complex 5 was administered; hereinafter referred to as C 5); and experimental group 11 (a group to which 100 mg/kg of complex 6 was administered; hereinafter referred to as C 6). Each test substance was administered once a day for a total of 4 weeks.

(2) Stress Induction

Stress was induced every day for 4 weeks from 7 days after administration of physiological saline to the negative control group and administration of the extract alone or each complex to experimental group 1, experimental group 2, experimental group 3, experimental group 4, experimental group 5 and experimental group 6. Stress induction was performed using a modification of the method of Willner et al. (Wilner et al., Reduction of sucrose preference by chronic unpredictable mild stress, 1987). Specifically, stress was induced by creating various unexpected psychological stressful situations, such as fasting, dietary restriction after fasting (feeding in small amounts), water supply cut off, provision of empty water bottles after water supply cut off, slanted cages, breeding of multiple experimental animals in one cage, flashing light, cold room, and continuous lighting.

(3) Forced Swimming Test

The experimental animals were subjected to a forced swimming test. After a cylindrical transparent water bath (14 cm diameter and 20 cm height) was filled with water at 23 to 25° C. so that the water depth was 15 cm, each experimental animal was put into the water bath. Each experimental animal was forced to swim in the cylindrical water bath for 6 minutes. 2 minutes after the start was considered an adaptation time, and during 4 minutes before the end, the total time during which each experimental animal was immobile in the cylindrical water bath (hereinafter referred to as "immobility time") was measured and recorded.

Specifically, the term "immobility time" refers to a state (immobility) in which there is no movement except for small movements such as raising the head above the water surface. Immobility is one of the indicators of depression, and can be commonly seen in stress-induced animals.

As shown in FIG. 1, it was confirmed that the immobility time of the negative control group (Control) was longer than that of the normal control group (Normal). On the other hand, it can be seen that the immobility time of experimental group 3 was slightly longer than that of the normal control group, but was shorter than (about 80% of) that of the negative control group. However, it was confirmed that the immobility times of experimental groups 4 and 5 showed a significant difference from that of the negative control group, and the immobility times of experimental groups 6, 7, 8, 9, 10 and 11, to which the complexes of the fermented and aged noni extract and the calamansi extract were administered, significantly decreased to about half of that of the negative control group. Therefore, it can be seen that the complex is more effective in reducing immobility time than the fermented and aged noni extract alone or the calamansi extract alone.

(4) Tail Suspension Test

The experimental animals were subjected twice to a tail suspension test. Each experimental animal was hung upside down for 6 minutes by holding the 1 cm tip of the tail at a height of 15 cm from the bottom, and the movement of the experimental animal was observed. 2 minutes after the start was considered an adaptation time, and during 4 minutes before the end, the time during which each experimental animal was immobile was measured and recorded.

Figure 2:
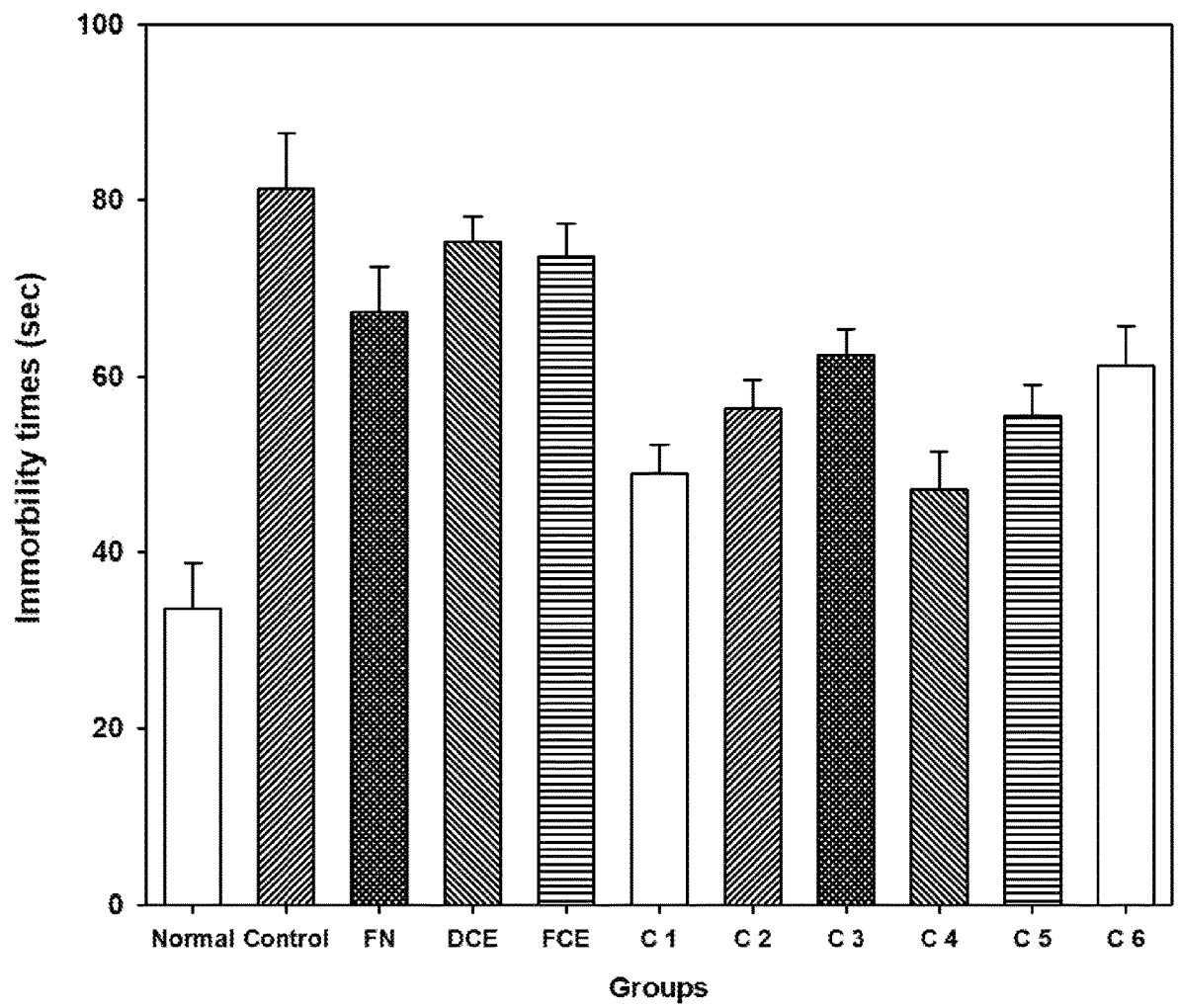
FIG. 2 is a graph showing the results of measuring the immobility times of experimental animals in a tail suspension test after intake of each of a control, a fermented and aged noni extract, a calamansi extract, and complexes of the fermented and aged noni extract and the calamansi extract in an experimental example of the present invention.

As shown in FIG. 2, it was confirmed that the immobility time of the negative control group (Control) in the state in which the animal was hung upside down was longer than that of the normal control group (Normal). This means that the immobility time was increased due to mental stress, suggesting that the frustration of the animals of the negative control group increased. The immobility time of experimental group 3 (FN) was short than (about 82% of) than that of the negative control group, suggesting that experimental group 3 tried to move the body relatively, but the immobility time of experimental group 4 was about 92% of that of the negative control group, which is a significant difference.

In addition, it was confirmed that the immobility times of the groups, to which each of complexes 1, 2, 3, 4, 5 and 6 produced by mixing the fermented and aged noni extract (FN) and the calamansi extract (DCE or FCE) together at a predetermined ratio was administered, were all significantly shorter than that of the negative control group. Therefore, it can be seen that the complex obtained by mixing the fermented and aged noni extract and the calamansi extract together at a predetermined ratio is more effective in alleviating stress induced lethargy and frustration.

Experimental Example 2: Test for Changes in Serum IgA Levels in Immobilization Stress-Induced Mice after Intake of Composition To immobilization stress-induced 8 week-old C57BL/6 mice in which stress was induced by immobilizing the mice in narrow frames for 2 hours every day for a total of 21 days, each of the fermented and aged noni extract (FN), the calamansi extract (CE), and complexes 1, 2, 3, 4, 5 and 6, produced by mixing the fermented and aged noni extract (FN) and the calamansi extract (DCE or FCE) together at a predetermined ratio, was orally administered every day at a dose of 100 mg/kg.

Figure 3:
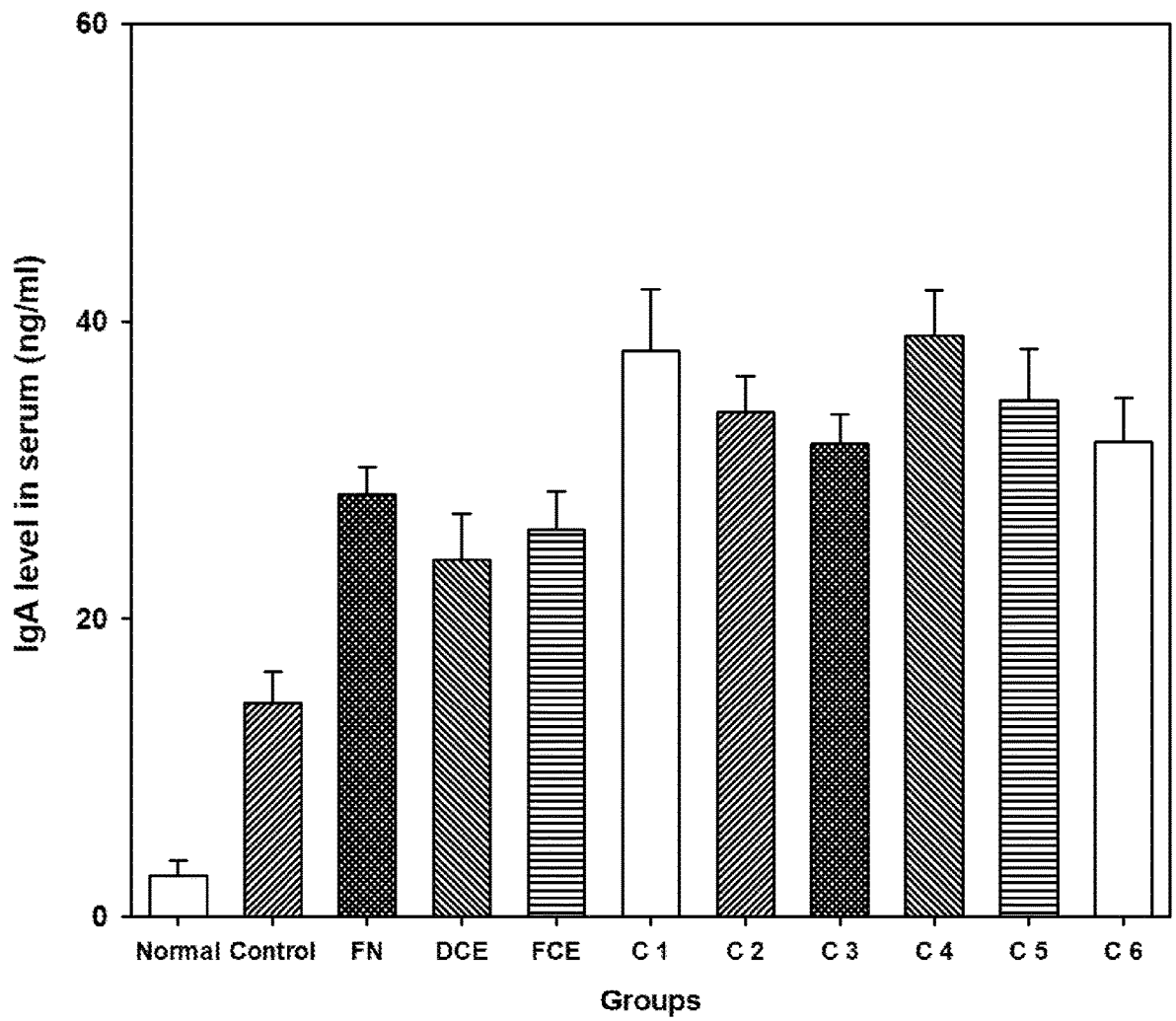
FIG. 3 is a graph showing the results of testing changes in the serum IgA levels in immobilization stress-induced mice after intake of each of a control, a fermented and aged noni extract, a calamansi extract, and complexes of the fermented and aged noni extract and the calamansi extract in an experimental example of the present invention.

As shown in FIG. 3, as a result of measuring the serum IgA levels, it was confirmed that the serum IgA levels in the groups, to which each of the fermented and aged noni extract (FN), complex 1 and complex 4 was administered, statistically significantly increased compared to that in the control group (Control).

In particular, the group to which complex 4 was administered showed the highest increase in the serum IgA level.

Experimental Example 3: Test for Changes in Body Weights of Immobilization Stress-Induced Mice after Intake of Composition To immobilization stress-induced 8 week-old C57BL/6 mice in which stress was induced by immobilizing the mice in narrow frames for 2 hours every day for a total of 21 days, each of the fermented and aged noni extract (FN), the calamansi extract (CE), and complexes 1, 2, 3, 4, 5 and 6, produced by mixing the fermented and aged noni extract (FN) and the calamansi extract (DCE or FCE) together at a predetermined ratio, was orally administered every day at a dose of 100 mg/kg.

Figure 4:
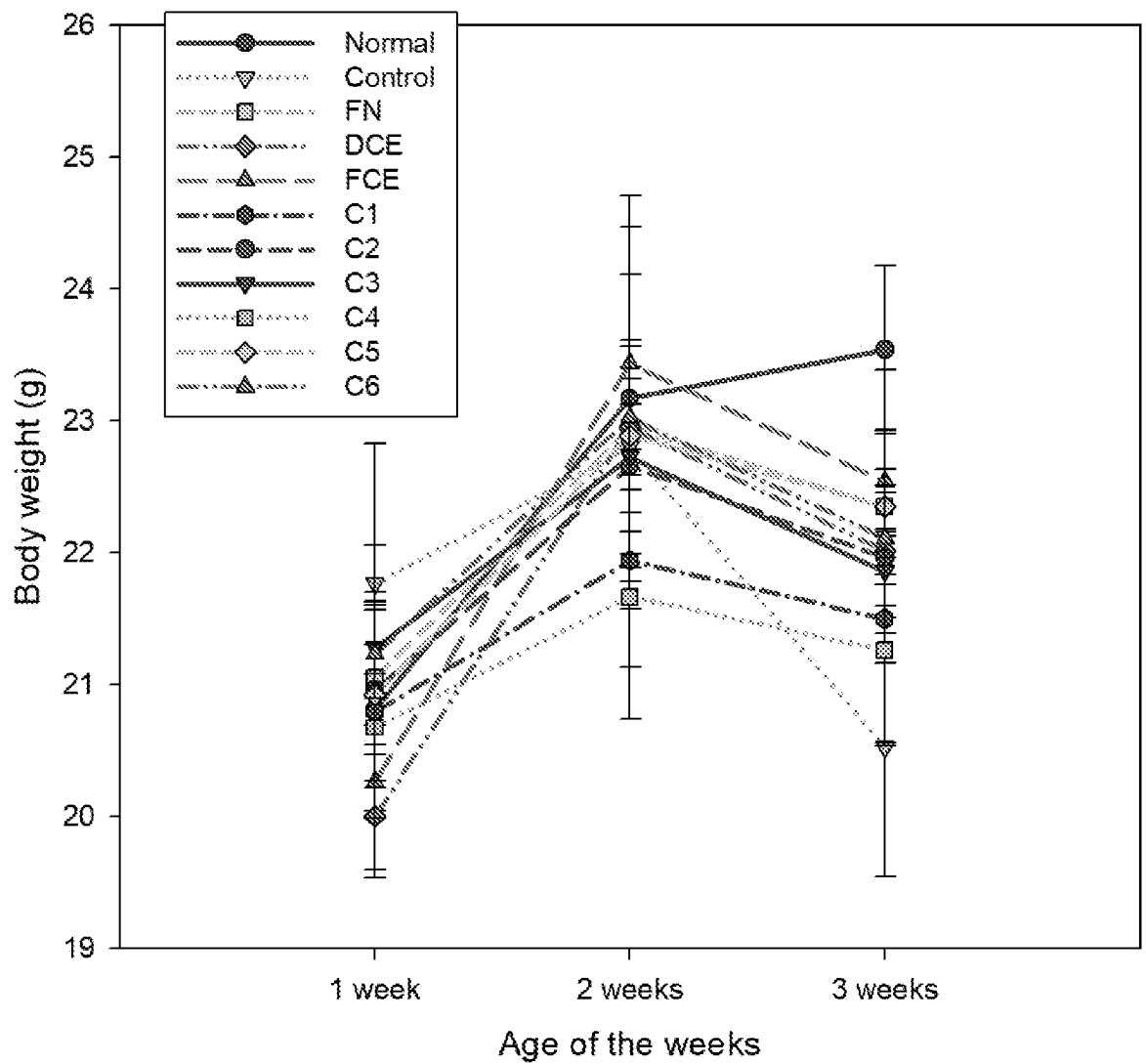
FIG. 4 is a graph showing the results of testing changes in the body weights of immobilization stress-induced mice after intake of each of a control, a fermented and aged noni extract, a calamansi extract, and complexes of the fermented and aged noni extract and the calamansi extract in an experimental example of the present invention.

As shown in FIG. 4, as a result of measuring the changes in body weight of the mice, it was confirmed that the immobilization stress-induced control group (Control) showed a weight loss compared to the normal group (Normal), and the weight losses of the groups, to which each of the fermented and aged noni extract (FN), complex 1 and complex 4 was administered, were smaller than that of the immobilization stress-induced control group (Control).

In particular, the groups to which each of complexes 1 and 4 was administered showed the lowest weight loss.

Experimental Example 4: Test for Changes in Serum Cortisol and Serotonin Levels in Immobilization Stress-Induced Mice after Intake of Composition To immobilization stress-induced 8 week-old C57BL/6 mice in which stress was induced by immobilizing the mice in narrow frames for 2 hours every day for a total of 21 days, each of the fermented and aged noni extract (FN), the calamansi extract (CE), and complexes 1, 2, 3, 4, 5 and 6 produced by mixing the fermented and aged noni extract (FN) and the calamansi extract (DCE or FCE) together at a predetermined ratio was orally administered every day at a dose of 100 mg/kg.

Figure 5:
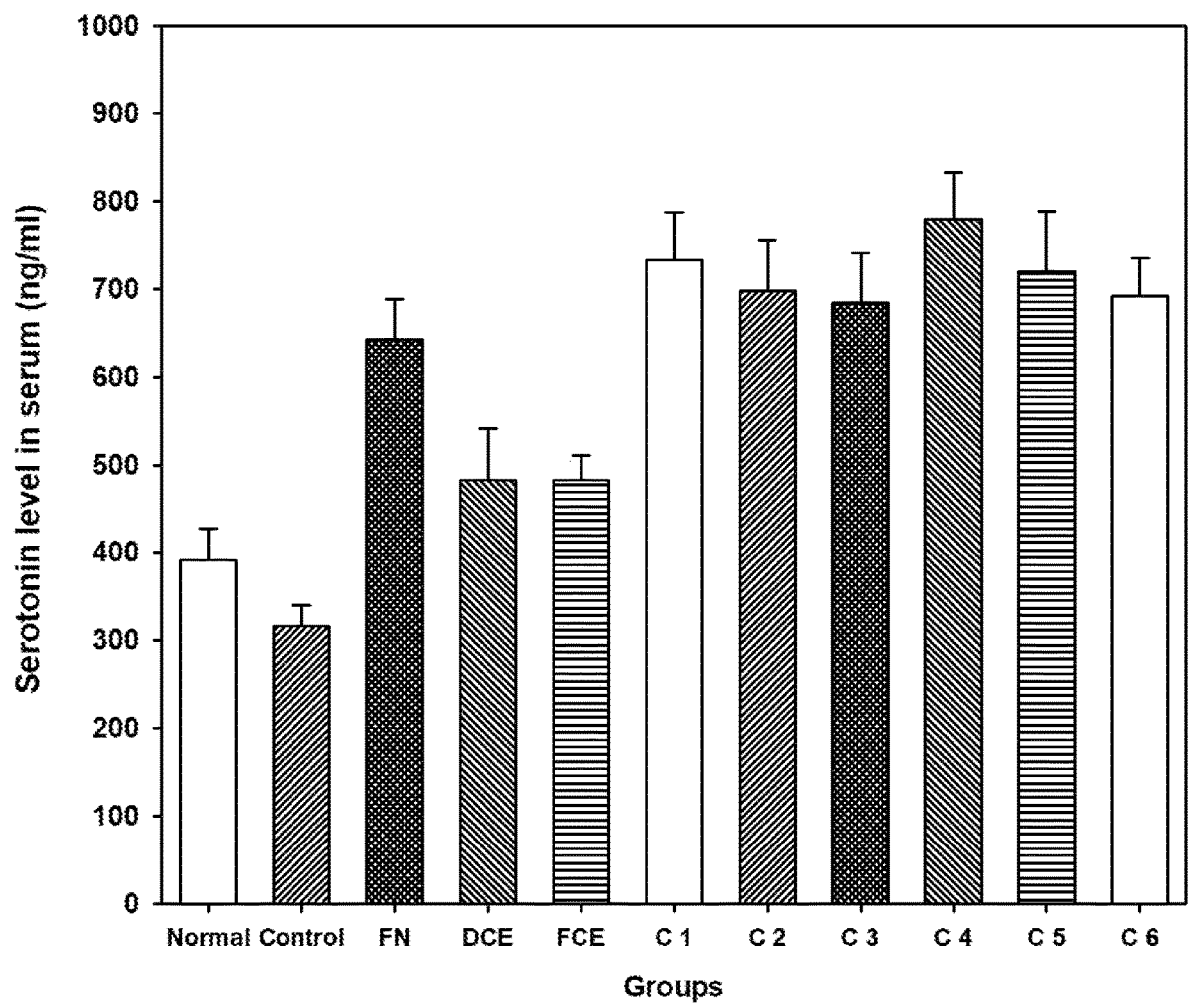
FIG. 5 is a graph showing the results of testing changes in the serum serotonin levels in immobilization stress-induced mice after intake of each of a control, a fermented and aged noni extract, a calamansi extract, and complexes of the fermented and aged noni extract and the calamansi extract in an experimental example of the present invention.

As a result of measuring the serum level of serotonin which is a hormone that makes the body feel happy, as shown in FIG. 5, it was confirmed that the groups, to which each of the fermented and aged noni extract (FN), complex 1 and complex 4 was administered at a dose of 100 mg/kg, showed a statistically significant increase in the serotonin level compared to the immobilization stress-induced group (Control) ($p<0.05$).

Figure 6:
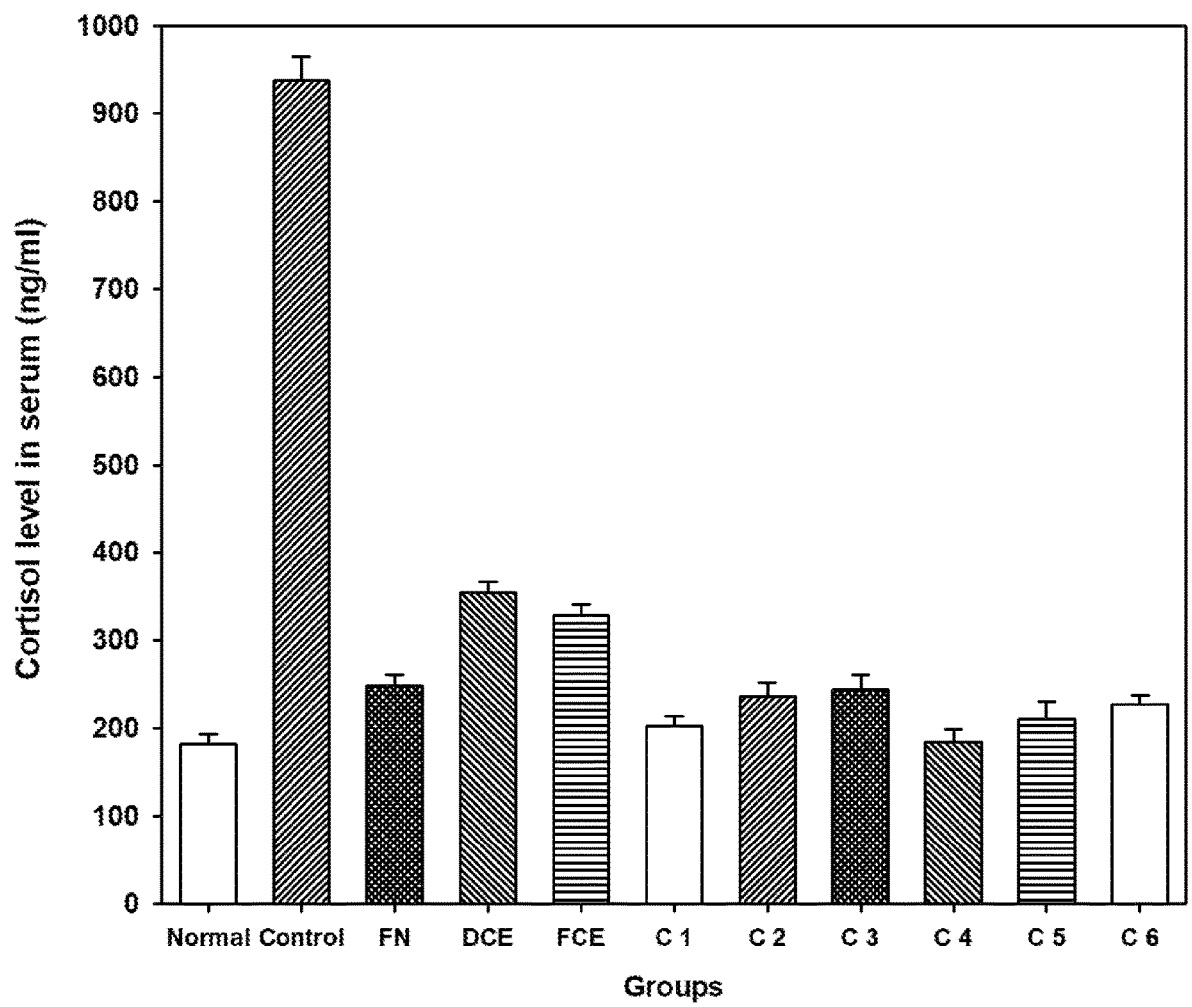
FIG. 6 is a graph showing the results of testing changes in the serum cortisol levels in immobilization stress-induced mice after intake of each of a control, a fermented and aged noni extract, a calamansi extract, and complexes of the fermented and aged noni extract and the calamansi extract in an experimental example of the present invention.

As a result of measuring the serum level of cortisol that is a stress hormone, as shown in FIG. 6, it was confirmed that the groups, to which each of the fermented and aged noni extract (FN), complex 1 and complex 4 was administered, showed a statistically significant decrease in the cortisol level compared to the immobilization stress-induced group (Control) ($p<0.05$).

In particular, the groups to which each of complexes 1 and 4 was administered showed the highest increase in the serotonin level and the highest decrease in the cortisol level.

While the present invention has been described with reference to the particular illustrative embodiments, those of ordinary skill in the art to which the present invention pertains will appreciate that the present invention may be embodied in other specific forms without departing from the technical spirit or essential characteristics of the present disclosure. Therefore, the embodiments described above are considered to be illustrative in all respects and not restrictive. The scope of the present invention should be defined by the claims rather than the foregoing description, and it should be understood that all modifications or variations derived from the meanings and scope of the present invention and equivalents thereof are included in the scope of the appended claims.

What is claimed is:

1. A food, pharmaceutical, or feed composition for relieving stress or inhibiting or treating stress-induced diseases containing, as active ingredients, fermented and aged noni or an extract thereof and a dried calamansi extract,
   wherein the fermented and aged noni is obtained through fermentation by inoculating noni fruit with lactic acid bacteria and aging by pouring fermentation broth produced in the fermentation over the noni fruit at regular time intervals; and
   the fermented and aged noni or its extract and the dried calamansi extract are contained at a weight ratio of 90:10.

2. The food, pharmaceutical, or feed composition of claim 1, which has any one formulation selected from the group consisting of powders, granules, pills, tablets, capsules, candy, syrups and beverages.

3. A pharmaceutical composition according to claim 1.

4. A feed composition according to claim 1.

* * * * *